United States Patent [19]

Samani

[11] Patent Number: 5,645,599

[45] Date of Patent: Jul. 8, 1997

[54] INTERSPINAL VERTEBRAL IMPLANT

[75] Inventor: Jacques Samani, St. Cyr Au Mont D'Or, France

[73] Assignee: Fixano, Bourg En Bresse, France

[21] Appl. No.: 635,735

[22] Filed: Apr. 22, 1996

[51] Int. Cl.$^6$ ............................ A61F 2/44; A61B 17/58
[52] U.S. Cl. ........................ 623/17; 606/53; 606/60; 606/61; 606/72
[58] Field of Search ........................ 623/17; 606/60, 606/61, 53, 72, 74

[56] References Cited

U.S. PATENT DOCUMENTS

| 5,092,866 | 3/1992 | Breard et al. ..................... 623/17 |
| 5,180,381 | 1/1993 | Aust et al. ........................ 623/17 |
| 5,180,393 | 1/1993 | Commarmond ................... 623/17 |
| 5,387,213 | 2/1995 | Breard et al. ..................... 623/17 |
| 5,395,372 | 3/1995 | Holt et al. ........................ 606/61 |
| 5,415,661 | 5/1995 | Holmes ............................. 623/17 |
| 5,496,318 | 3/1996 | Howland et al. ................. 606/61 |

FOREIGN PATENT DOCUMENTS

| 0650620 | 11/1991 | Australia ......................... 623/17 |
| 0322334 | 6/1989 | European Pat. Off. ........... 623/17 |
| 2681525 | 3/1993 | France . |
| 3113142 | 1/1982 | Germany . |
| 1484348 | 6/1989 | U.S.S.R. .......................... 606/72 |

*Primary Examiner*—John G. Weiss
*Assistant Examiner*—Tram Anh T. Nguyen
*Attorney, Agent, or Firm*—Oliff & Berridge

[57] ABSTRACT

This implant comprises a substantially U-shaped body having an elastic flexibility in the area of its central portion, and two pairs of brackets projecting from the outer face of the two branches of the body, these brackets defining stirrups for receiving the spinous processes of the vertebrae and comprising means permitting them to be fixed to the processes.

7 Claims, 2 Drawing Sheets

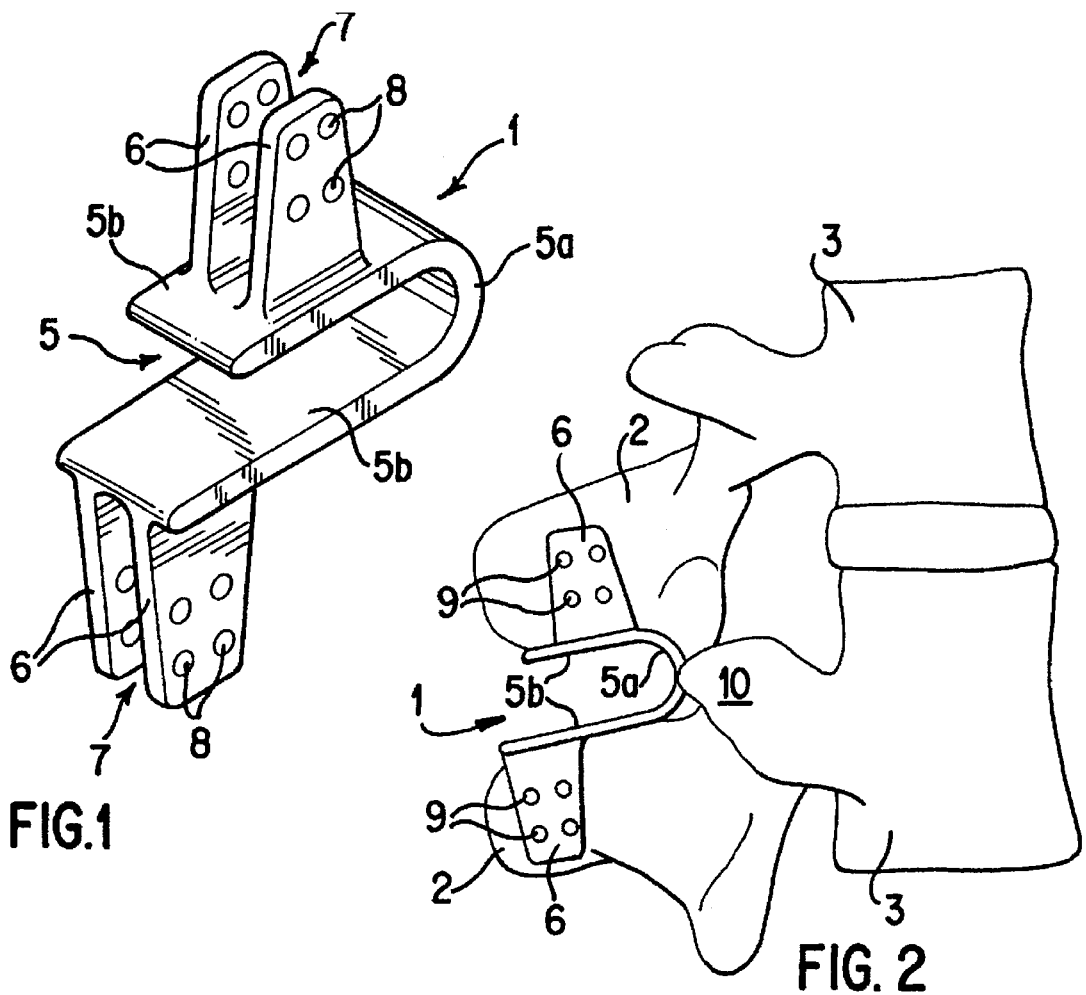
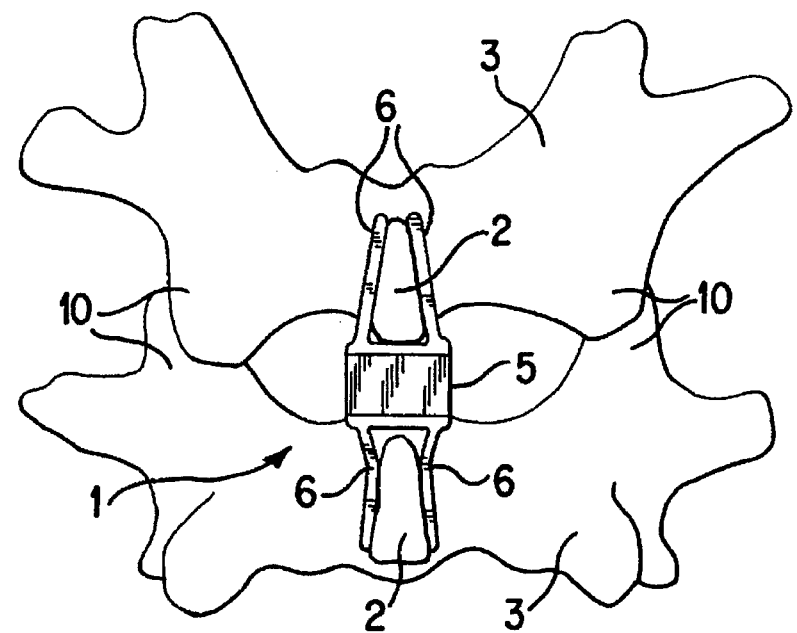

INTERSPINAL VERTEBRAL IMPLANT

The present invention relates to an interspinal vertebral implant, that is to say an implant intended to be inserted between the spinous processes of two contiguous vertebrae.

BACKGROUND OF THE INVENTION

Damage to an intervertebral disk can lead to abnormal play of the vertebrae contiguous to this disk. This play subjects the posterior articular processes to considerable stresses, generating very painful wear and tear of these processes and general instability of the spinal column.

Such instability can also result from an operation performed on a herniated intervertebral disk, which has entailed access to the disk, in other words a weakening of the ligament system of the articulation, or can result from certain cases of arthrosis which also subjects the posterior articulations to considerable and painful stresses.

DESCRIPTION OF THE PRIOR ART

To rectify this instability, it is known to implant devices for bracing the spinal column, these devices comprising rigid elements which are connected to means of osseous anchoring.

The rigid elements frequently consist of metal rods which are implanted along several vertebrae, on either side of the spinous processes. The means for osseous anchoring generally consist of screws, which are called "pedicle" screws because they are implanted in the area of the pedicles of the vertebrae.

These devices have the disadvantage that they are difficult to implant, and in particular necessitate considerable and complex work in putting them into place. Moreover, and in particular, they immobilize a relatively long vertebral segment, which significantly reduces the mobility of the patient and may subject the articulations situated on either side of this rigid segment to considerable stresses which are capable of generating new pathological conditions.

It is known to rectify an instability of the spinal column by provision of a wedge which is inserted between the spinous processes.

Such a wedge may be implanted in particular at one end of the segment of the spinal column rigidified by an osteosynthesis device as mentioned above, in order to guarantee a relative support of the vertebrae and to limit the stresses to which they are subjected.

An existing wedge comprises an interspinal bearing cushion which is fixed to the spinal column by a textile ligament which surrounds the processes.

Upon extension of the spinal column, the bearing cushion makes it possible to maintain a minimum spacing between the processes of the two vertebrae and thus to relieve the stress on the intervertebral disk as well as the posterior articulations. Upon flexion of the spinal column, the ligament limits the spacing apart of the two processes.

This bearing cushion, also made of textile material, has the disadvantage of being relatively rigid and thus of holding the vertebrae in a specific position, scarcely comfortable for the patient. In addition, it tends to wear under the influence of the repeated stresses to which it is subjected.

The need to pass the ligament around the processes involves operating in healthy anatomical areas in order to form a passage, and weakening the natural ligaments. Moreover, it is difficult to determine the appropriate tensioning to give to the ligament in order to control the possibility of play of the processes in relation to the bearing cushion. In addition, the ligament becomes worn under the effect of the repeated stresses which the processes exert upon it, and it also tends to slacken, which promotes this wear and reduces the limitation on the movement of the vertebrae upon flexion of the spinal column.

SUMMARY OF THE INVENTION

The present invention aims to remedy all these shortcomings by making available an interspinal implant which provides for a flexible positioning of the vertebrae in relation to one another, acting in an anatomical manner comfortable for the patient, which is not subject to wear, even under the influence of repeated stresses, and which can be put into place simply, easily and quickly, without the need to operate on healthy anatomical areas.

To this end, the implant to which the invention relates comprises a substantially U-shaped body having an elastic flexibility in the area of its central portion, and two pairs of brackets projecting from the outer face of the two branches of the body, these brackets defining stirrups for receiving the spinous processes of the vertebrae and comprising means permitting them to be fixed to the processes.

This implant is intended to be inserted in the interspinal space, with said central portion lying in the area of the posterior articular processes, with said branches lying against the spinous processes, and with each pair of brackets engaging around a spinous process.

By virtue of the flexibility of the central portion of its body, the implant provides for a flexible positioning of the vertebrae in relation to one another. It permits a flexion and an extension of the spinal column on either side of a neutral position corresponding to the substantially parallel position of the two branches of its U-shaped body.

The limit of elasticity of this central portion makes it possible to prevent excessive lordosis and thus prevents considerable stresses from being exerted on the posterior articulations, without in so doing preventing any extension movement of the spinal column. This limit of elasticity also makes it possible to limit the flexion of the spinal column, without recourse to a ligament.

The implant according to the invention thus acts in an anatomical manner and is comfortable for the patient.

It is made of a strong material and does not suffer any wear under the influence of repeated stresses.

In addition, by virtue of its specific shape and its fixing brackets, it can be put into place by simple engagement in the interspinal space, without requiring special work at the site receiving it. In the case of a herniated intervertebral disk in particular, the interspinal space has often been prepared during the hernia operation. Once this preparation has been performed, it suffices to move the spinous processes of the two vertebrae concerned slightly apart, to engage the implant between them by inserting the spinous processes between the aforementioned pairs of brackets, and to fix the implant to the processes. Thus, the implant does not require any intervention in healthy anatomical areas.

A bearing cushion made of suitable elastic material, either woven material or synthetic material, can be put into place between the branches of the U-shaped body in order to limit the closing together of these two branches and to ensure a supplementary cushioning of the vertebrae, should this prove necessary.

This implant is preferably made of a metal material forged in one piece. It is advantageously made of titanium. In addition to its suitable mechanical characteristics, this material permits postoperative radiography techniques, such as the body scanner or nuclear magnetic resonance, where it does not interfere with the images.

According to a preferred embodiment of the invention, the pairs of brackets are offset in relation to one another along the branches of the body, in such a way that several successive implants can be put into place on several consecutive vertebrae. This offset arrangement in fact makes it possible to engage the brackets of two adjacent implants on the same spinous process.

The means for fixing the implants to the spinous processes of the vertebrae preferably consist of holes for receiving screws or crimped spikes engaged in the processes.

For its complete understanding, the invention is described once more hereinbelow with reference to the attached diagrammatic drawing which represents, by way of a nonlimiting example, a preferred embodiment of the interspinal implant to which the invention relates.

BRIEF DESCRIPTION OF THE DRAWING

FIG. 1 is a perspective view of the implant;

FIG. 2 is a side view thereof, following implantation;

FIG. 3 is a rear view thereof, following implantation;

DESCRIPTION OF THE PREFERRED EMBODIMENT

Figure 4:
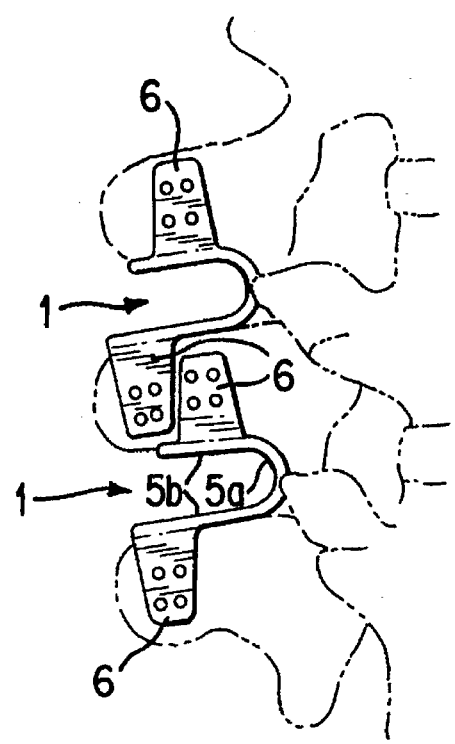
FIG. 4 is a side view of two wedges which are intended to be implanted on three consecutive vertebrae.

The figures represent, from different angles, an interspinal vertebral implant 1, that is to say an implant which is intended to be inserted between the spinous processes 2 of two contiguous vertebrae 3.

The implant 1 comprises a substantially U-shaped body 5 having an elastic flexibility in the area of its central portion 5a, and two pairs of brackets 6 projecting from the outer face of the two branches 5b of the body 5.

The implant 1 is made of titanium and is forged in one piece.

As can be seen from the figures, each pair of brackets 6 defines a stirrup 7 for receiving the spinous processes 2. FIG. 3 shows more particularly that the two brackets 6 of the upper branch converge toward one another in the direction of their free end, whereas the two brackets 6 of the lower branch 5b converge in an initial phase toward one another and then diverge in the direction of their free end. This specific configuration of the brackets 6 allows them to adapt to the anatomical configuration of the spinous processes 2 inserted between them.

In addition, each bracket 6 comprises holes 8 which are intended to receive bone screws 9, or spikes engaged in the processes and crimped in these holes 8, permitting the brackets 6 to be fixed to the spinous processes 2.

Figure 5:
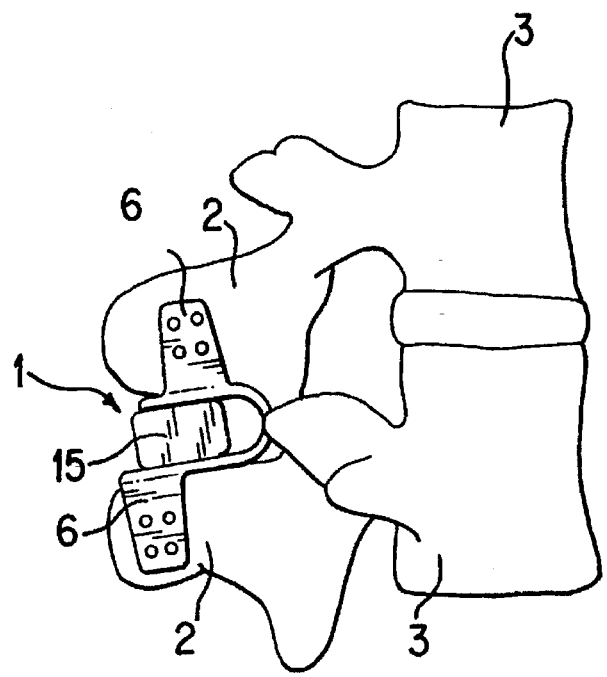
FIG. 5 is a side view thereof, following implantation, in accordance with an alternative embodiment.

As is shown more particularly by FIGS. 2 and 5, the implant 1 is intended to be inserted in the interspinal space, with said central portion 5a of the body 5 lying in the area of the posterior articular processes 10, with said upper and lower branches 5b lying against the spinous processes 2, and with each pair of brackets 6 engaging around one of the spinous processes 2.

By virtue of the flexibility of the central portion 5a, the implant provides for a flexible positioning of the vertebrae 3 in relation to one another. It permits a flexion and an extension of the spinal column on either side of a neutral position represented in FIGS. 2 and 3, corresponding to the substantially parallel position of the two branches 5b.

The limit of elasticity of the central portion 5a makes it possible to prevent excessive lordosis, and thus prevents considerable stresses from being exerted on the posterior articulations 10, without in so doing preventing any extension movement of the spinal column. This limit of elasticity also makes it possible to limit the flexion of the spinal column, without recourse to a prosthetic ligament engaged around the spinous processes 2.

The implant 1 thus acts in an anatomical manner and is comfortable for the patient.

By virtue of its specific shape and its fixing brackets 6, it can be put into place by simple engagement in the interspinal space, necessitating only limited work in the site receiving it. In an operation on a herniated intervertebral disk, in particular, the interspinal space has often been prepared during the operation on the hernia in order to permit access to the disk. Once this preparation has been performed, it suffices to move the spinous processes 2 slightly apart from one another, to engage the implant 1 between them by inserting the processes 2 in the stirrups 7, and to fix the implant to the processes 2 by the abovementioned screws 9 or spikes.

The implant is preferably made of titanium. It does not suffer any wear under the influence of the repeated stresses to which it is subjected. In addition to having suitable mechanical characteristics, titanium permits the use of radiography techniques such as the body scanner or nuclear magnetic resonance following the operation. This is because it does not interfere with the images obtained.

FIG. 4 shows that the pairs of brackets 6 are offset in relation to one another along the branches 5b of the body 5, in such a way that several successive implants 1 can be put into place on several consecutive vertbrae of the spinal column. This offset arrangement allows the brackets 6 of two contiguous implants 1 to be engaged on the same spinous process 2. The implant according to the invention can therefore be used as a replacement for the conventional devices for bracing a segment of the spinal column, without this segment being rendered completely rigid.

FIG. 5 shows that a bearing cushion 15 of suitable elastic material, either woven material or synthetic material, can be put into place between the upper and lower branches of the body 5 and can be fixed to these by any suitable means, for example by adhesive bonding. This bearing cushion 15 makes it possible to limit the closing together of the two upper and lower branches and to ensure a supplementary cushioning of the vertebrae 3, should this prove necessary.

We claim:

1. An interspinal vertebral implant comprising:
   a U-shaped body having a central portion and two branches, wherein at least the central portion is elastically flexible;
   two pairs of brackets, wherein each pair of brackets projects from an outer face of one of the two branches, and wherein each pair of brackets comprises a stirrup for receiving a spinous process of a vertebrae; and
   means wherein said brackets includes for attaching the brackets to spinous processes of the vertebrae.

2. The implant as claimed in claim 1, further comprising a bearing cushion made of a suitable elastic material, which is either a woven material or a synthetic material, said bearing cushion being located between the branches of the U-shaped body.

3. The implant as claimed in claim 1, wherein the U-shaped body is made of a metal material forged in one piece.

4. The implant as claimed in claim 3, wherein the U-shaped body is made of titanium.

5. The implant as claimed in claim 1, wherein the pairs of brackets are offset in relation to one another along the branches of the body, in such a way that several successive implants can be put into place on several consecutive vertebrae.

6. The implant as claimed in claim 1, wherein the means for attaching the brackets to the spinous processes of the vertebrae comprise a plurality of holes for receiving screws or crimped spikes that engage the processes.

7. The implant as claimed in claim 1, wherein the pair of brackets projecting from an upper branch of the U-shaped body converge toward one another in the direction of their free ends, and wherein the pair of brackets projecting from a lower branch of the U-shaped body converge in an initial phase toward one another and then diverge in the direction of their free ends.

* * * * *

UNITED STATES PATENT AND TRADEMARK OFFICE
CERTIFICATE OF CORRECTION

PATENT NO. : 5,645,599
DATED : July 8, 1997
INVENTOR(S) : Jacques Samani

It is certified that error appears in the above-identified patent and that said Letters Patent is hereby corrected as shown below:

Column 4,
Line 61, "means wherein said brackets includes for attaching the" should read -- wherein said brackets include means for attaching the --.

Signed and Sealed this

Eighteenth Day of January, 2005

JON W. DUDAS
*Director of the United States Patent and Trademark Office*